United States Patent [19]
Kato et al.

[11] Patent Number: 5,006,514
[45] Date of Patent: Apr. 9, 1991

[54] α,α-TREHALOSE TRIMYCOLATES AND PHARMACEUTICAL COMPOSITIONS

[75] Inventors: Yoshiko Kato, Kobe; Junji Yoshinaga, Neyagawa; Takeshi Shogaki, Suita; Satoko Kurano, Okaka; Ikuya Yano, Minoh, all of Japan

[73] Assignee: Sawai Pharmaceutical Co., Ltd., Osaki, Japan

[21] Appl. No.: 123,933

[22] PCT Filed: Mar. 19, 1987

[86] PCT No.: PCT/JP87/00171
§ 371 Date: Oct. 2, 1987
§ 102(e) Date: Oct. 2, 1987

[87] PCT Pub. No.: WO87/05606
PCT Pub. Date: Sep. 24, 1987

[30] Foreign Application Priority Data

Mar. 20, 1986 [JP] Japan .................... 61-63004
Aug. 28, 1986 [JP] Japan .................... 61-203486

[51] Int. Cl.[5] .................... A61K 31/71; A61K 31/70; C07H 13/06
[52] U.S. Cl. .................... 514/53; 536/18.2; 536/115; 536/119; 536/53; 435/100; 514/25
[58] Field of Search .................... 514/53, 25; 536/18.2, 536/53, 115, 119; 435/100

[56] References Cited

U.S. PATENT DOCUMENTS

| | | | |
|---|---|---|---|
| 4,243,663 | 1/1981 | Azuma et al. | 536/119 |
| 4,307,229 | 12/1981 | Liav et al. | 536/115 |
| 4,454,119 | 6/1984 | Fukushi | 514/53 |
| 4,612,304 | 9/1986 | Fukushi | 536/115 |
| 4,684,719 | 8/1987 | Nishikawa et al. | 536/115 |

FOREIGN PATENT DOCUMENTS

| | | | |
|---|---|---|---|
| 3248167 | 6/1984 | Fed. Rep. of Germany | 435/100 |
| 59-157097 | 9/1984 | Japan | 536/119 |

OTHER PUBLICATIONS

Azuma et al.; J. Nat. Cancer Inst., 52(1):95–101, Jan. 1974.
Lederer; Chemistry and Physics of Lipids, 16:91–106, 1976.
Rapp et al.; J. Gen. Microbiol., 115:491–503, 1979.
Liav et al.; Carbohyd. Res., 125:323–328, 1984.
Shimakata et al.; Arch. Biochem. Biophys., 238(2):497–508, May 1985.
Butler et al.; J. Clin. Microbiol., 23(1):182–185, Jan. 1986.
Tomiyasu et al.; FEBS Letters, 203(2):239–242, Jul. 1986.
Butler et al.; J. Clin. Microbiol., 25(1):2126–2131, Nov. 1987.
Gendre et al.; Bull. Soc. Chim., France, (1956), pp. 1478–1482.

*Primary Examiner*—Ronald W. Griffin
*Assistant Examiner*—Nancy S. Carson
*Attorney, Agent, or Firm*—Berman, Aisenberg & Platt

[57] ABSTRACT

An α,α-trehalose trimycolate represented by formula:

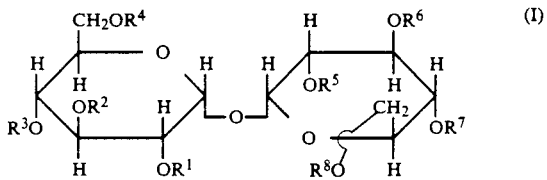

(wherein $R^1$ through $R^8$ each represents a hydrogen atom or mycolic acid residue, and three of $R^1$ through $R^8$ are mycolic acid residues; these mycolic acid residues may, or may not be identical with each other).

Since the said α,α-trehalose trimycolate possesses both immunopotentiating activity and antitumor activity on animals and is low in toxicity, it is expected to be applied to a protective drug against infection of various microbes, an antitumor agent and immunopotentiation at the time of decline in physical strength.

17 Claims, 7 Drawing Sheets

α,α-TREHALOSE TRIMYCOLATES AND PHARMACEUTICAL COMPOSITIONS

FIELD OF THE INVENTION

The present invention relates to novel α,α-trehalose trimycolates and pharmaceutical compositions which are useful as pharmaceuticals.

BACKGROUND OF THE INVENTION

It is already known that when a microbe of the genus Arthrobacter, Corynebacterium, Nocardia or Mycobacterium, capable of utilizing a sugar, such as glucose, fructose, sucrose or trehalose, to produce a lipid containing any of these sugars is cultured in a medium whose main carbon source is any of these sugars under aerobic conditions, it accumulates the glycolipid in bacterial cells or in the medium, and the mycolic acid ester of glucose, fructose, sucrose or trehalose can be obtained by recovering the accumulated glycolipid [Japanese Published and Unexamined Patent Application No. 48186/1975, Japanese Published and Unexamined Patent Application No. 3514/1978, Japanese Published and Unexamined Patent Application No. 89632/1984 and the Journal of the National Cancer Institute, 52, 95–101 (1974)].

It is also known that when a microbe capable of utilizing hydrocarbons is cultured in a medium whose carbon sources are various n-paraffins, trehalose lipid can be obtained. (Japanese Published and Examined Patent Application No. 7349/1972).

However, these glycolipids are mono- or dimycolic acid esters; when the sugar is glucose, for example, the glycolipid is the mycolic acid ester thereof at C(6-position)-OH; when the sugar is fructose, the glycolipid is the mycolic acid ester thereof at C(1-position)-OH or C(6-position)-OH, or both. In addition, even in case the sugar is the disaccharide, sucrose or trehalose, only the monomycolic acid ester thereof at C(6-position)-OH and the dimycolic acid ester thereof at C(6-position)-OH and C(6'-position)-OH are known

DISCLOSURE OF THE INVENTION

Taking note of these facts, the present inventors made investigations and found that bacteria of the genus Rhodococcus produce a glycolipid which is entirely different from conventional glycolipids. The present inventors isolated this component and made a structural analysis thereof. Also analyzed were the number of the mycolic acid molecules bonded to the sugar and the bond sites by gas chromatography/mass spectrometry (hereinafter abbreviated to GC/MS). As a result, it was confirmed that this glycolipid is a compound in which 3 molecules of mycolic acid are esterified at the specific sites in α,α-trehalose. Based on these findings, the present inventors developed the present invention.

The present invention relates to:

① the α,α-trehalose trimycolates [hereinafter also referred to as trimycolic acid ester (I)] represented by the formula:

(wherein $R^1$ through $R^8$ each represents a hydrogen atom or mycolic acid residue, and three of $R^1$ through $R^8$ are mycolic acid residues; these mycolic acid residues may, or may not be identical with each other), and ② pharmaceutical compositions consisting of the trimycolic acid ester (I) and any one or more of pharmacologically allowable additives.

In the formula (I), the mycolic acid residues represented by $R^1$ through $R^8$ are residues having the basic structure represented by the formula:

(wherein R' represents a straight or branched alkyl group having 8 to 26 carbon atoms with some 0 to 2 unsaturated bonds; R" represents a straight or branched aliphatic group having 20 to 60 carbon atoms (with some 1 to 9 unsaturated bonds) and the unsaturated bonds are normally double bonds. In the trimycolic acid ester (I) of the present invention, it is not necessary for the three mycolic acid residues of $R^1$ through $R^8$ to be all identical with each other; they may be different from each other.

However, the mycolic acid residues which can be collected from bacteria of the genus Rhodococcus are mainly those having a total of 60 to 80 carbon atoms. In addition, the most important biochemical feature of the mycolic acid residues contained in the trimycolic acid ester (I) obtained from bacteria of the genus Rhodococcus is that they are high in the degree of unsaturation, which is suitable for low temperature conditions; this becomes more noticeable, for example, when the bacterium is grown at low temperature in obtaining the trimycolic acid ester (I) from the bacterium.

Particularly preferable compounds for the present invention include the following:

① The compound of the formula (I) wherein $R^1$, $R^2$ and $R^8$ are mycolic acid residues, and $R^3$, $R^4$, $R^5$, $R^6$ and $R^7$ are hydrogen atoms.

② The compound of the formula (I) wherein $R^1$, $R^4$ and $R^8$ are mycolic acid residues, and $R^2$, $R^3$, $R^5$, $R^6$ and $R^7$ are hydrogen atoms.

The trimycolic acid ester (I) of the present invention is produced, for example, by culturing a bacterium of the genus Rhodococcus, specifically *Rhodococcus aurantiacus* (ATCC 25938) to allow the bacterium to produce the said compound mainly in bacterial cells, and collecting the compound mainly from the bacterial cells.

In this cultivation, any medium can be used, as long as it is a conventionally known synthetic medium or medium using natural substances, which can be used for the cultivation of microbes of the genus Rhodococcus. For example, glucose, trehalose, etc., can be used as carbon sources for the cultivation. Substances which can be used as nitrogen sources include inorganic nitrogen compounds, such as potassium nitrate, sodium nitrate, ammonium nitrate, ammonium sulfate and ammonium phosphate; and organic nitrogen compounds, such as peptone, meat extract and corn steep liquor. Salts of sodium, potassium, calcium, zinc, magnesium, manganese, phosphoric acid, etc., as minerals, and vitamins, amino acids, or yeast extract rich in these substances as growth promotors, may be added as appropriate.

A culturing pH of 5 to 9, specifically 7 to 7.5, is appropriate, and a culturing temperature of 10° to 40° C., specifically 25° to 30° C., is appropriate. Cultivation is carried out by means of liquid culture or solid culture under aerobic conditions. About 3 to 14 days of cultivation is normally appropriate, during which the glycolipid with 3 molecules of mycolic acid being esterified with α,α-trehalose is normally produced in bacterial cells.

To obtain the trimycolic acid ester (I) from the bacterial cells thus obtained, ordinary methods of collecting bacterial component are used. For example, the trimycolic acid ester (I) can be collected on the basis of the characteristics of the desired product in solvent extraction, adsorption, elution, methods based on the difference of solubility, ionic bond strength, etc., used alone or repeatedly, or in any appropriate combination.

For example, the desired product can be fractionally collected by extracting the cultured bacterial cells with an organic solvent, such as ether, chloroform or a mixed solution of chloroform and methanol (2:1, v/v), and subjecting the resulting extract to silica gel column chromatography, thin layer chromatography, or DEAE cellulose column chromatography using a simple or mixed solvent of chloroform, methanol, acetone, acetic acid, water, etc., as a developing solvent. As to the crude lipid or fraction, the fraction insoluble in methanol or acetone but soluble in diethyl ether may be collected for further purification.

To analyze the structure of the trimycolic acid ester(I) thus obtained, a purified sample thereof is subjected to IR spectrometry and hydrolysis or methanolysis; the structure of the sugar and the composition of the mycolic acid can be known by analyzing by GC or GC/MS the sugar after conversion into a trimethylsilyl ester derivative and the mycolic acid after conversion into a trimethylsilyl etherified methyl ester. The number of the mycolic acid molecules bonded to the sugar and the bond sites can also be known by sequentially carrying out the complete methylation, hydrolysis, decomposition to monosaccharides, reduction and acetylation of the sample by ordinary methods, then carrying out a GC/MS analysis of the resulting partially methylated alditol acetate.

Test example 1 (granuloma formation test)

The trimycolic acid ester (I) was tested for immunostimulatory activity in accordance with the method of Yamamoto et al. [Immunology, 40, 557-564 (1980)]. A 0.15 M phosphate-buffered saline (pH 7.0), the equal volume of Freund's incomplete adjuvant (manufactured by Difco Laboratories) and the trimycolic acid ester (I) (GL-1 or GL-2) obtained in Example 1 were mixed together, and homogenized using a homogenizer, then a physiological saline solution containing 0.2% of the surface active agent Tween 80 (manufactured by Wako Pure Chemicals) was added until the final oil concentration became 3.2% to prepare a water-in-oil-in-water emulsion. 0.2 ml of this emulsion was administered via the tail vein to each of 9 to 10 male ICR line mice in each group.

One week later, lungs and spleens were excised, and calculations were made of the percent ratios by weight of the lungs and spleens to body weight. In Table 1, Control group represents a group administered an emulsion containing no glycolipid, and the amount of the glycolipid administered to each mouse of the glycolipid administration groups was 300 μg. The figures in the table represent mean value ± standard error.

TABLE 1

| Group | Lungs | Spleens |
|---|---|---|
| Non-administration group | 0.598 ± 0.008 | 0.521 ± 0.016 |
| Control group | 0.619 ± 0.023 | 0.509 ± 0.028 |
| GL-2 administration group | 1.959 ± 0.117 | 1.583 ± 0.096 |
| GL-1 administration group | 1.605 ± 0.072 | 1.212 ± 0.085 |

As is obvious from Table 1, granulomas were formed in lungs and spleens by the administration of the trimycolic acid ester (I) GL-1 or GL-2.

Reference was then made to Infection and Immunity, 29 (1), 30-35 (1980) and 10 (5), 1044-1050 (1974), and it was suggested that this substance possesses immunopotentiating activity and antitumor activity.

Test example 2 (antitumor test)

To each mouse transplanted Sarcoma-180 or Meth A cells subcutaneously via the inguinal region GL-2, in an emulsion as described in Test example 1, was administered intravenously via the tail vein 3 times/week at a dose of 25 μg/10 g body weight/day × 10 times starting on the next day of the transplantation. As a result, GL-2 showed solid tumor growth inhibition ratios as shown in Table 2.

TABLE 2

| | (Growth Inhibition) | | | |
|---|---|---|---|---|
| | No administration (%) | GL-2 (%) | Control (%) | GL-2 (%) |
| Sarcoma-180 | 0 | 57.1 | 0 | 51.5 |
| Meth A | 0 | 48.0 | 0 | 53.8 |

Materials and methods (i) Animals: ICR line 3w, female (Clea Japan)(for Sarcoma-180) BALB/c line 5w, male (Shizuoka Animal Farm)(for Meth A)

The above mice were used in the experiment after 1 week of preliminary breeding.

(ii) Tumors: Sarcoma-180 and Meth A

In both cases, ascites was collected 1 week after the intraperitoneal transplantation, and it was diluted with a sterilized physiological saline solution to $2 \times 10^7$ cells/ml, after which it was transplanted subcutaneously via the inguinal region at a dose of 0.05 ml ($1 \times 10^6$ cells)/mouse. The day of the transplantation was taken as the 0-day.

(iii) Trimycolic acid ester (I):

GL-2 was prepared as a 250 μg/ml w/o/w emulsion, and administered intravenously via the tail vein (3 times/week) at a dose of 0.1 ml (25 μg)/10 g body weight × 10 times, starting on the 1-day.

(iv) Controls:

2 groups, namely, non-administration control group and w/o/w control group administered a w/o/w emulsion alone in the same manner as in (iii).

(v) Evaluation of the effects:

On the 25th day tumor nodes were excised and weighed, and the tumor growth inhibition ratios were calculated. Each group consisted of 10 mice.

Test example 3 (toxicity test)

The trimycolic acid ester (I) (GI-1 or GL-2), in an emulsion as described in Test example 1, was administered to male ICR line mice (10 mice for each group) to determine the $LD_{50}$ values.

In the case of intravenous administration, the $LD_{50}$ values of the trimycolic acid ester (I) were >50 mg/kg for GL-1 and >25 mg/kg for GL-2; in the case of intraperitoneal administration, the values were >50 mg/kg for GL-1 and >25 mg/kg for GL-2.

When intravenously administered in a liposome of egg yolk phosphatidylcholine-bovine brain phosphatidylserine (7:3, molar ratio), GL-2 showed an $LD_{50}$ value of >380 mg/kg.

Compared with the lethal toxicity level of trehalose dimycolate as obtained by reference to Infection and Immunity, 24 (2), 586–588 (1979), the Journal of the National Cancer Institute, 52 (1), 95–101 (1974) and the European Journal of Biochemistry, 87, 497–504 (1978), the toxicity of this substance was found to be low.

As shown above, the trimycolic acid ester (I) of the present invention possesses both immunopotentiating activity and antitumor activity on animals, including humans, horses, bovines, swine, rats, mice and guinea pigs, and is low in toxicity; it is therefore expected to be applied as a protective drug against infection of various microbes, as an antitumor agent and, at the time, for immunopotentiation with regards to decline in physical strength.

Though it varies with different diseases, routes of administration, degrees of seriousness, tolerances to the drug, etc., the dose of the trimycolic acid ester (I) is normally 10 mg to 2 g /adult/day, preferably 500mg to 1 g, administered singly or in several times.

The trimycolic acid ester (I) can be prepared into any pharmaceutical preparation by common methods of preparing pharmaceuticals. Therefore, the present invention also provides pharmaceutical compositions containing the trimycolic acid ester (I). Such pharmaceutical compositions are prepared by routine methods using arbitrary, necessary and pharmaceutically allowable additives (e.g. carriers and excipients). As examples of pharmaceutical preparations, mention may be made of oral drugs (e.g. tablets, capsules, powders and liposomes) and injections [liposomes, emulsifying injections {using an emulsifier (e.g. organic acids, organic bases, surface active agents, water-soluble polymers and water-soluble organic solvents)}, suspending injections (using physiological saline solution, etc.)]. As an example of particularly preferable dosage form, mention may be made of liposome preparation.

Liposome preparations can be prepared by known methods. The following method is a specific example thereof:

That is, a liposome preparation is produced using an ordinary homogenizer (e.g. pressure jet homogenizer and ultrasonic homogenizer). In this method, a liposome preparation can be easily produced by first mixing together and heating the required amounts of an oil or fat ingredient (e.g. vegetable oil such as soybean oil), phospholipid and the trimycolic acid ester (I), and, if necessary, a known emulsification aid, emulsion stabilizer, isotonizing agent, etc., to prepare a solution, homogenizing the resulting solution using a homogenizer to prepare a water-in-oil dispersion, then adding the required amount of water thereto and re-homogenizing the dispersion to an oil-in-water emulsion [refer to J. Am. Oil Chem. Soc., 32, 365–370 (1950)]. The liposome preparation may be provided as a liquid preparation without any after-treatment, and may also be provided as a dry preparation after lyophilization. In the case of lyophilized preparation, it is normally diluted or dispersed in distilled water for injection, etc. before use.

The present invention is hereinafter described in more detail with some examples.

EXAMPLE 1

*R. aurantiacus* (ATCC 25938) was inoculated to 5 ml of a medium (pH 7.2) composed of 1% glucose, 0.5% peptone, and 0.2% yeast extract, and cultured at 28° to 30° C. for 4 days (preculture). 1 ml of the resulting culture was inoculated to a medium (pH 7.2) composed of 1% glucose, 0.5% peptone, 0.2% yeast extract and 1.5% agar in a plate form, and cultured at 28° to 30° C. under aerobic conditions for 5 days. About 1.5 g (wet weight) of bacterial cells were thus obtained. By repeating the above-mentioned procedure, 100 g (wet weight) of bacterial cells were collected, after which they were washed with water, and subjected to high speed agitation using a waring blender in 4 l of an added mixed solution of chloroform-methanol (2:1, v/v). 800 ml of water was then added, and the lower layer of the two separated layers was collected fractionally. A mixed solution of chloroform-methanol (2:1, v/v) was further added, and the lower layer was collected. These two collected lower layers were combined together, and concentrated using a rotary evaporator to obtain 1.2 g of a crude lipid. This crude lipid showed in TLC at least 4 main spots assigned to glycolipids. These main spots were designated as GL-1, GL-2, GL-3, GL-4, etc., in a descending order of Rf value. This crude lipid was then dissolved in chloroform, and the insoluble matters were filtered; the resulting solution was injected into a silica gel column (2.5 cm$\phi$×20 cm). Chromatograms were developed with 150 ml chloroform, 150 ml of a mixed solution of chloroformethanol (97:3, v/v), 150 ml of a mixed solution of chloroform-acetone (1:1, v/v), 200 ml acetone, 200 ml of a mixed solution of chloroform-methanol (2:1, v/v) and 200 ml of methanol in this order; the fraction in which GL-2, which ranked 2nd highest in Rf value, was detected by thin layer chromatography was collected and concentrated, then the acetone-insoluble matters were collected and spotted in a band on a silica gel plate (Analtech "Silica Gel G" plate, 20×20 cm). Chromatograms were developed with a mixed solution of chloroform-methanol-acetone-acetic acid (90:10:6:1, v/v). The band containing GL-2 was taken, and extracted with a mixed solution of chloroform-methanol (2:1, v/v), after which it was concentrated to dryness under reduced pressure to obtain 6.1 mg of a colorless pasty substance. The data of physical and chemical properties of this substance are as follows:

Molecular weight: About 3500 (determined by gel filtration)

Specific rotation $[\alpha]_D^{24}=41.15$ to 41.57 (c=0.01, chloroform)

Melting point: Unmeasurable

Figure 1:
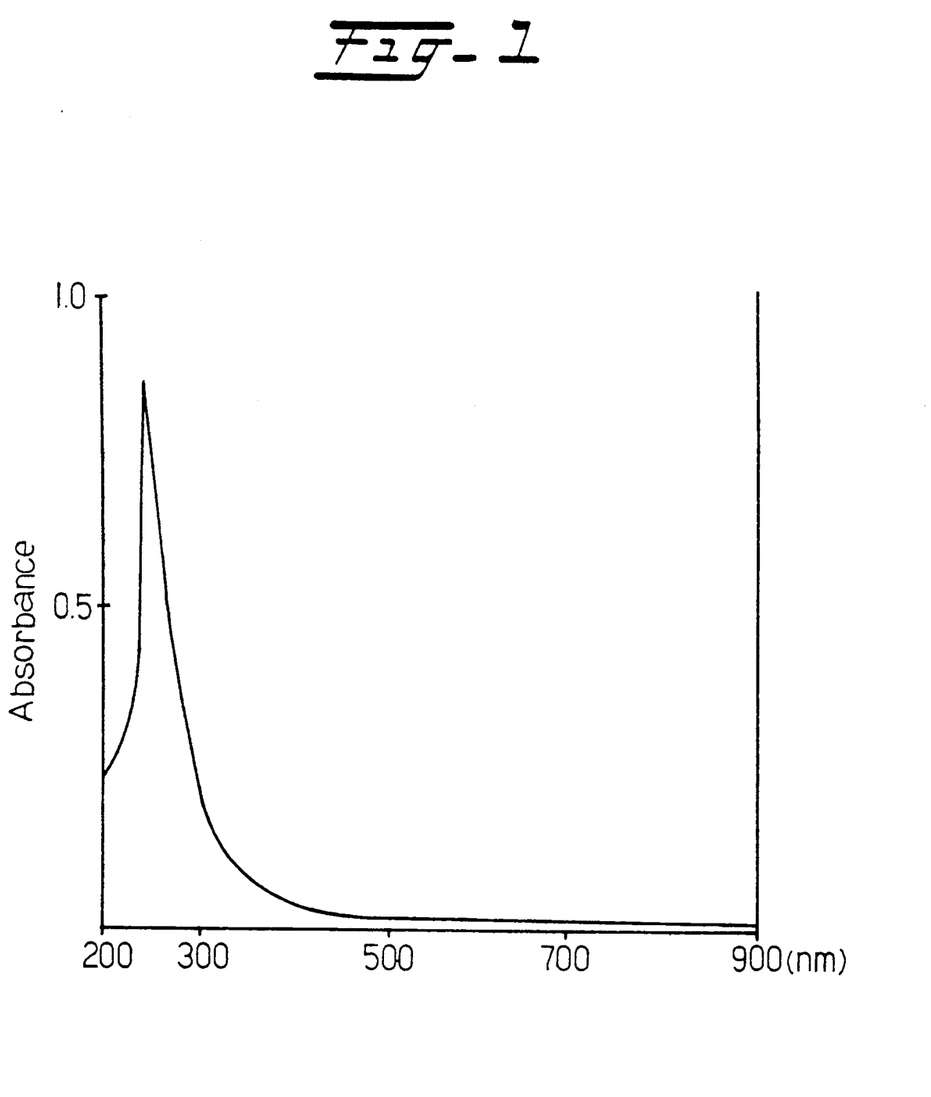
FIG. 1, FIG. 2 and FIG. 3 show the visible radiation-/ultraviolet absorption spectrum of GL-2, the infrared absorption spectrum of GL-2, and NMR spectrum of GL-2 respectively.

Visible radiation/UV absorption spectrum: Absorption peak appeared near 245 nm (see FIG. 1).

Figure 2:
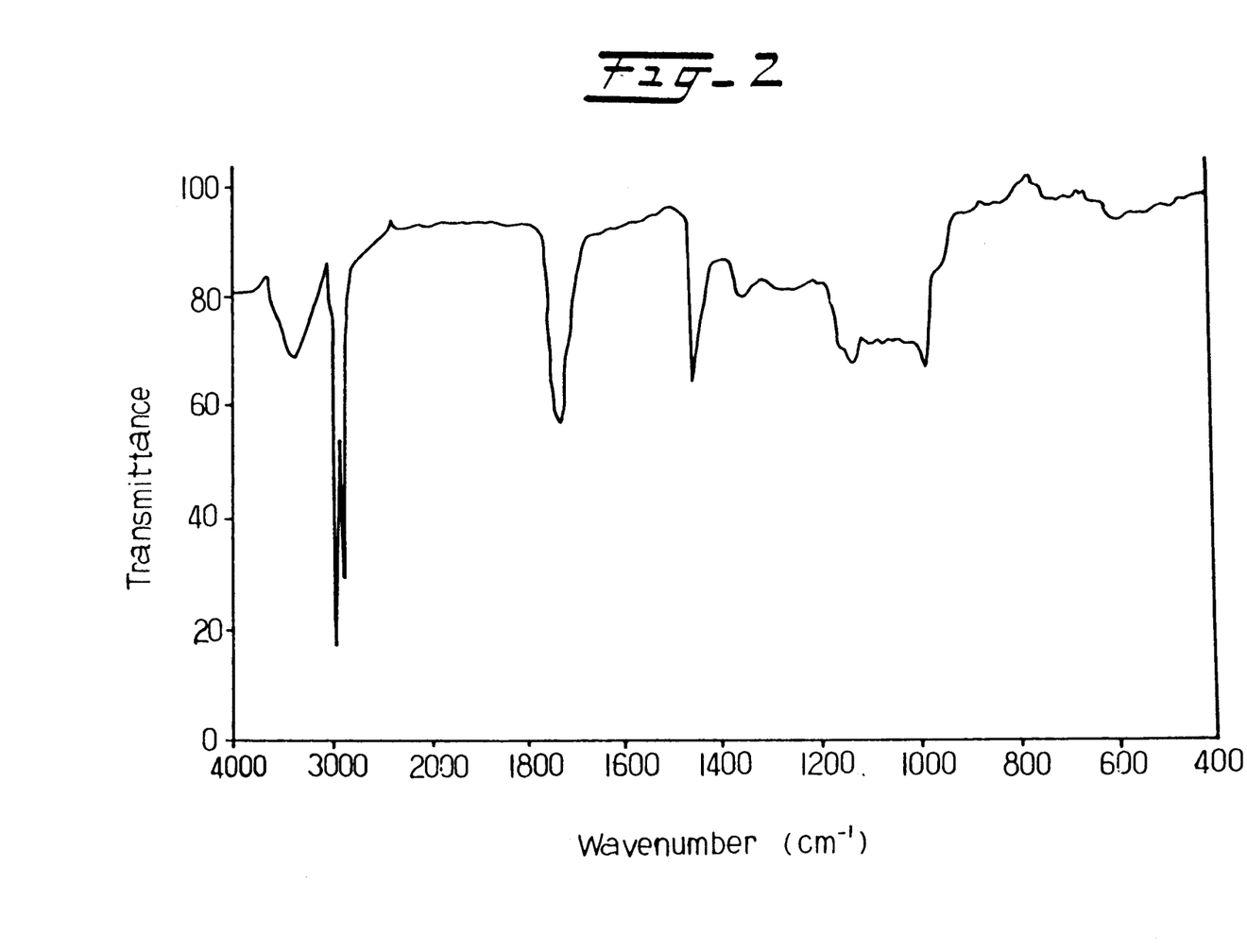

Infrared absorption spectrum: (see FIG. 2)

Figure 3:
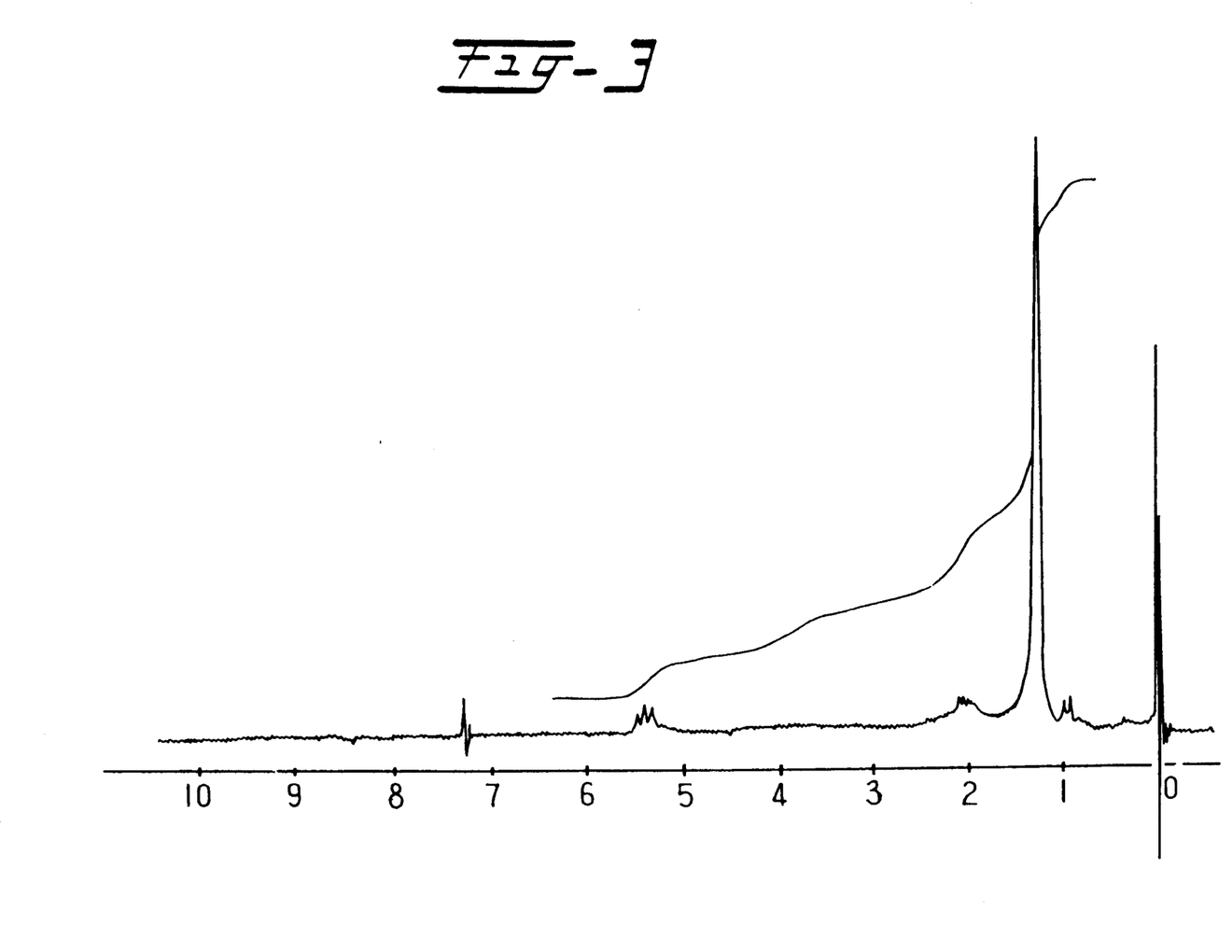

NMR spectrum Measured in $CDCl_3$ (see FIG. 3).

Solubility: Soluble in chloroform, hexane, diethyl ether, chloroform-methanol (2:1), benzene and pyridine. Insoluble in acetone, methanol, ethanol, dimethyl sulfoxide and water.

Color reaction: Positive for anthrone-sulfuric acid reaction and α-naphthol-sulfuric acid reaction.

Acidity, neutrality, or alkalinity: Neutral

Rf value in thin layer chromatography: 0.42 to 0.60 (Analtech "silica Gel G" plate was used.) Developing solvent: Mixed solution of chloroform-methanol-acetone-acetic acid (90:10:6:1, v/v)

A structural analysis of this GL-2 was conducted as follows:

To 1 mg of GL-2 was added 1 ml of 0.1 N sodium hydroxide [solution in chloroform-methanol (1:2, v/v)], and this was followed by hydrolysis at room temperature for 6 hours, then 1 ml of chloroform and 2 ml of 0.2 N hydrochloric acid were added; the resulting mixed solution was partitioned to 2 layers. The chloroform layer was concentrated to dryness. To the resulting concentrate 2 ml of benzene-methanol-sulfuric acid (10:20:1, v/v) was added, and methyl esterification was carried out at 90° C. for 2 hours. 2 ml water and 2 ml hexane were then added; the resulting hexane layer was concentrated to dryness, after which it was dissolved in a small amount of hexane. The resulting solution was developed with a mixed solution of hexane-diethyl ether (4:1, v/v) using a silica gel plate as mentioned above, and this was followed by the separation and recovery of the hexane layer. 150 μl of N,O-bis(trimethylsilyl)trifluoroacetamide-pyridine (2:1, v/v) was then added, and the reaction followed at 70° C. for 30 minutes. The reaction product was then evaporated to dryness using a rotary evaporator while adding 2 ml benzene several times, then a small amount of hexane was added, and a GC/MS analysis was carried out.

Based on the results thus obtained, it was proved that the mycolic acid residue of GL-2 has the structure of the formula (II) wherein R' is a straight or branched alkyl group having 8 to 26 carbon atoms with some 0 to 1 unsaturated bond, and R" is a straight or branched alkyl group having 20 to 60 carbon atoms with some 1 to 7 (nearly 6, for the main component) unsaturated bonds.

Figure 4:
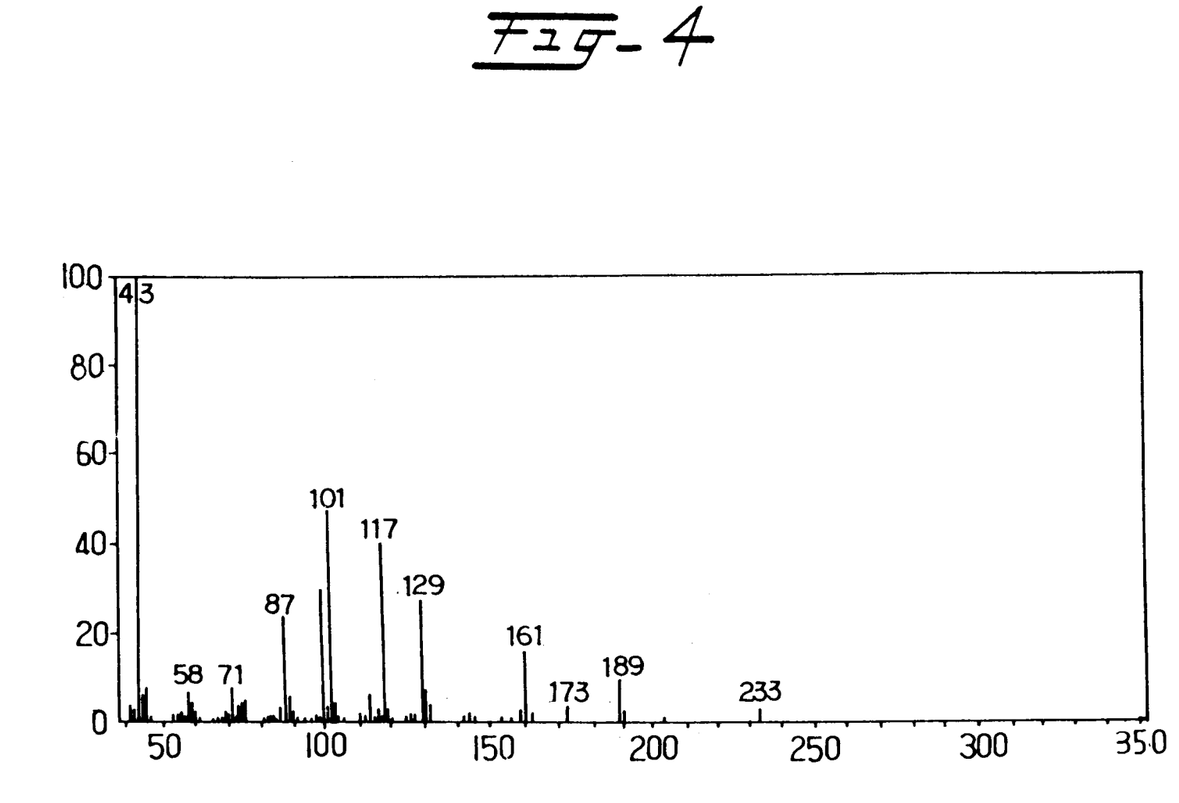
FIG. 4 and FIG. 5 show the MS spectrum of 2,3,4-tri-o-methylglycitol acetate and the MS spectrum of 4,6-di-o-methylglycitol acetate, respectively.
Figure 5:
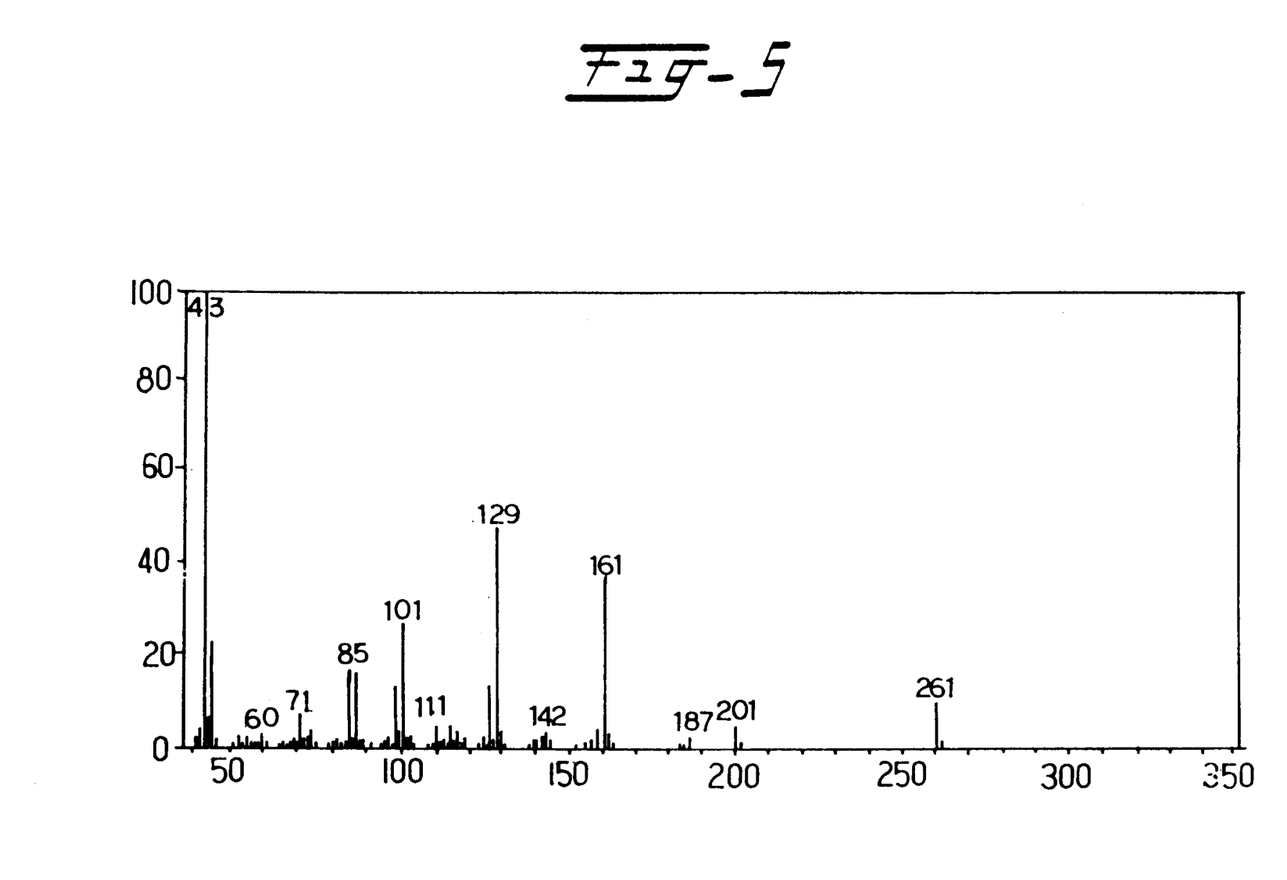

GL-2 was further subjected to complete methylation with diazomethane-boron trifluoride etherate, ester hydrolysis with potassium hydroxide, decomposition to monosaccharides with 4% hydrochloric acid (solution in methanol) and 2 N trifluoroacetic acid, reduction with sodium borohydride, and then acetylation with pyridine-acetic anhydride (1:1); the resulting partially methylated alditol acetate was analyzed by GC/MS. As a result, 2,3,4-tri-o-methylglycitol acetate (see FIG. 4) and 4,6-di-o-methylglycitol acetate (see FIG. 5) were obtained in a ratio of nearly 1:1; GL-2 was thus found to have the structure of α,α-trehalose 2,3,6'-trimycolate.

EXAMPLE 2

Chromatograms were developed by silica gel chromatography in the same manner as in Example 1; the fraction in which GL-1, which ranked first highest in Rf value, was detected in thin layer chromatography was collected and concentrated, after which it was collected fractionally by thin layer chromatography in the same manner as in Example 1 [developing solvent: chloroform-methanol-acetone-acetic acid (90:10:6:1, v/v)] to obtain 1.0 mg of GL-1 in the form of a colorless pasty substance. This substance was analyzed in the same manner as in Example 1; it was found that the mycolic acid residue of GL-1 is almost identical with that of GL-2, and GL-1 has the structure of α,α-trehalose-2,6,6'-trimycolate.

It is inferred that GL-3 and GL-4 mentioned in Example 1 are di- or monomycolic acid esters. The date of physical and chemical properties of GL-1 are as follows:

Molecular weight: About 3500 (determined by gel filtration)

Melting point: Unmeasurable

Figure 6:
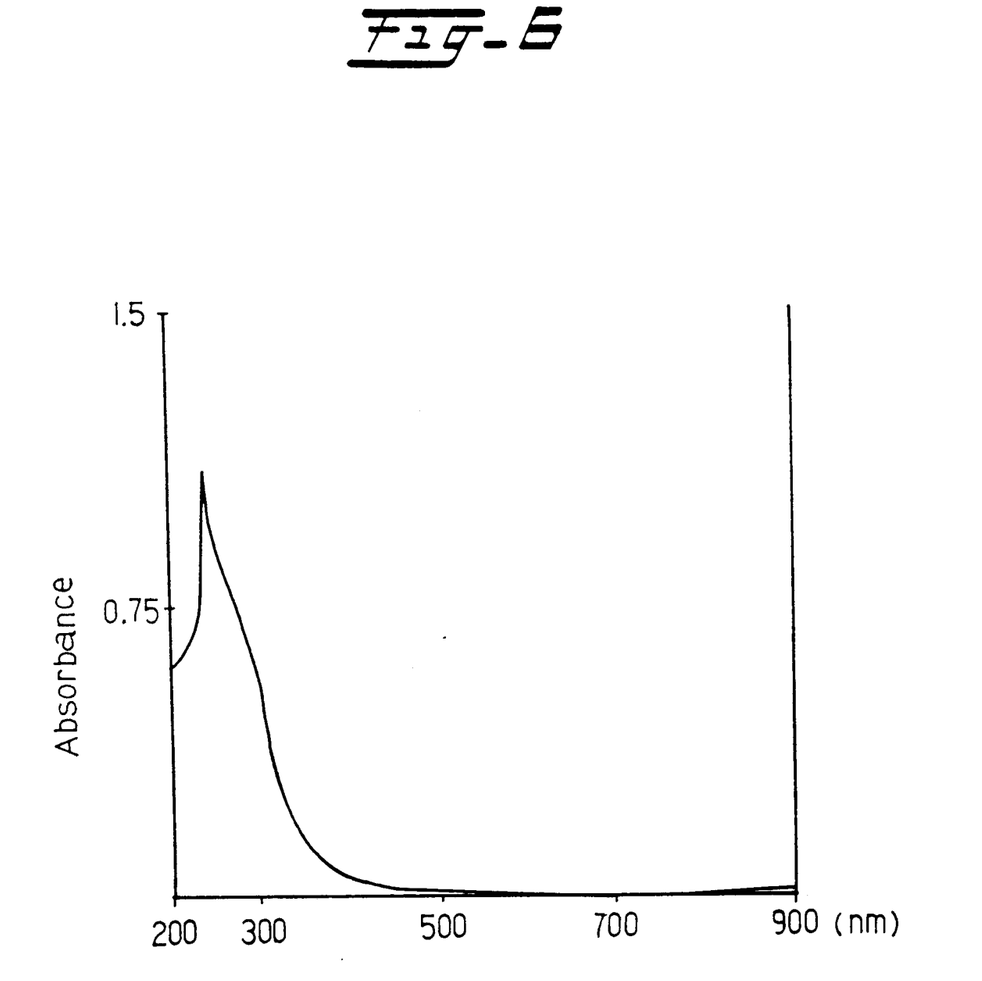
FIG. 6 and FIG. 7 show the visible radiation/ultraviolet absorption spectrum of GL-1 and the infrared absorption spectrum of GL-1, respectively.

Visible radiation/UV absorption spectrum: (see FIG. 6).

Figure 7:
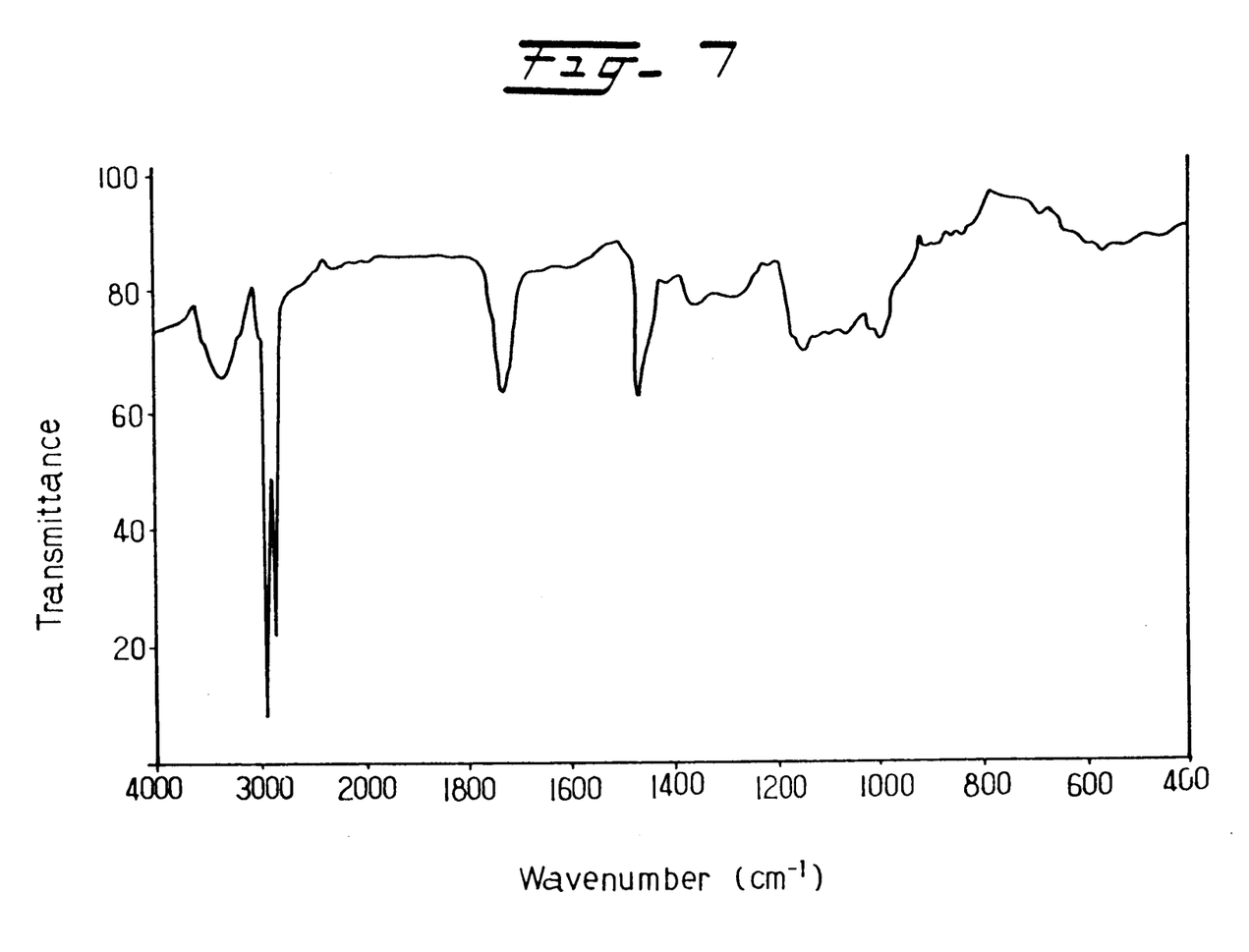

Infrared absorption spectrum: (see FIG. 7)

Solubility: Same as GL-2 (see Example 1)

Color reaction: Positive for anthrone-sulfuric acid reaction and α-naphthol-sulfuric acid reaction.

Acidity, neutrality, or alkalinity: Neutral

Rf value in thin layer chromatography: 0.73 to 0.80 (Analtech "silica Gel G" plate was used.) Developing solvent: Mixed solution of chloroform-methanol-acetone-acetic acid (90:10:6:1, v/v)

EXAMPLE 3

1 ml of the culture obtained by preculture in the same manner as in Example 1 was inoculated to 300ml of a medium (pH 7.2) composed of 1% glucose, 0.5% peptone and 0.2% yeast extract, and subjected to shaking culture at 30° C. for 5 days to obtain 4 g of bacterial cells, which were then treated in the same manner as in Example 1 to obtain 170 mg of a crude lipid. This crude lipid was then treated in the same manner as in Examples 1 and 2 to obtain 38.8 mg of α,α-trehalose-2,3,6'-trimycolate and 29.8 mg of α,α-trehalose-2,6,6'-trimycolate.

EXAMPLE 4

Except that shaking culture was carried out at 10° C. for 14 days, the same procedure as in Example 3 was followed to obtain α,α-trehalose-2,3,6'-trimycolate and α,α-trehalose-2,6,6'-trimycolate.

It was proved that, in the trimycolic acid residues of the formula (II) in the above-mentioned trimycolic acid residues (I) thus obtained, R' is a straight or branched alkyl group having 8 to 26 carbon atoms with some 0 to 2 unsaturated bonds, and R" is a straight or branched alkyl group having 20 to 60 carbon atoms with some 2 to 9 unsaturated bonds.

EXAMPLE 5

A liposome-suspended injection of the following formulation was prepared by a routine method.

| GL-2 | 300 mg |
|---|---|
| Egg yolk phosphatidylcholine | 720 mg |
| Physiological saline solution | appropriate amount |
| Entire amount | 5 ml |

EXAMPLE 6

An injection using a non-aqueous solvent, of the following formulation was prepared by a routine method.

| GL-2 | 100 mg |
|---|---|
| Olive oil | appropriate amount |
| Entire amount | 1 ml |

EXAMPLE 7

The specified amounts of the following components except water were taken, and agitated with warming to 40° C. to prepare a homogeneous emulsion. To this emulsion purified water was added, and this was followed by agitation to prepare a turbid emulsive injection.

| Bulk drug (GL-2) | 300 mg |
|---|---|
| Olive oil | 100 mg |
| dl-α-tocopherol | 50 mg |
| Polysorbate 80 | 80 mg |
| Sorbitan sesquioleate | 60 mg |
| Purified water | Appropriate amount |
| Entire amount | 5 ml |

We claim:

1. An α,α-trehalose trimycolate represented by the formula:

wherein each of $R^1$, $R^2$ and $R^8$ is the same or a different mycolic
acid residue, and each of $R^3$, $R^4$, $R^5$, $R^6$ and $R^7$ is a hydrogen atom.

2. An α,α-trehalose trimycolate as defined in claim 23 which is the same as that obtained from bacteria of the genus Rhodococcus.

3. An α,α-trehalose trimycolate according to claim 2, which is an extract of Rhodococcus bacteria.

4. A bacterial extract according to claim 3 wherein the α,α-trehalose trimycolate has from 60 to 80 carbon atoms.

5. An antitumor pharmaceutical composition consisting essentially of an effective amount of a compound defined in claim 1 and pharmacologically acceptable additive.

6. A pharmaceutical composition as defined in claim 5 in dosage form and which comprises an antitumor agent.

7. A pharmaceutical composition as defined in claim 5 which is in the form of a liposome.

8. An α,α-trehalose trimycolate according to claim 1 wherein each mycolic acid residue is of the structure wherein R' is straight-chain or branched aliphatic hydrocarbyl group having from 8 to 26 carbon atoms and from 0 to 2 unsaturated bonds, R" is a straight-chain or branched aliphatic group having from 20 to 60 carbon atoms and from 1 to 9 unsaturated bonds.

9. An α,α-trehalose trimycolate according to claim 8 wherein any unsaturated bond is a double bond.

10. A bacterial extract which consists essentially of an α,α-trehalose trimycolate according to claim 8.

11. A pharmaceutical composition which comprises an antitumor effective amount of trimycolate according to claim 10 and pharmacologically-acceptable additive.

12. An α,α-trehalose trimycolate according to claim 1, the mycolic acid residues of which have a total of from 60 to 80 carbon atoms.

13. A substantially pure α,α-trehalose trimycolate which is non-synthetic and is a trimycolate according to claim 1.

14. The trimycolate according to claim 1 which has the visible radiation/ultraviolet absorption spectrum of FIG. 1, the infrared absorption spectrum of FIG. 2 and the NMR spectrum of FIG. 3.

15. A pharmaceutical composition which comprises an antitumor effective amount of trimycolate according to claim 14 and pharmacologically-acceptable additive.

16. A method of inhibiting susceptible tumor growth in a mammal which comprises administering to the mammal an effective amount of a compound according to claim 1.

17. A method according to claim 16 wherein the susceptible tumor is one having susceptibility to the compound similar to that of Sarcoma-180 or that of Meth A.

* * * * *